United States Patent [19]
Farris et al.

[11] Patent Number: 5,209,751
[45] Date of Patent: May 11, 1993

[54] SPINAL FIXATION SYSTEM

[75] Inventors: Robert A. Farris, Memphis, Tenn.; David L. Brumfield, Nesbit, Miss.

[73] Assignee: Danek Medical, Inc., Memphis, Tenn.

[21] Appl. No.: 838,498

[22] Filed: Feb. 19, 1992

[51] Int. Cl.$^5$ .................... A61B 17/56; A61B 17/00
[52] U.S. Cl. ........................................ 606/61; 606/73
[58] Field of Search ............................. 606/61, 69-71

[56] References Cited

U.S. PATENT DOCUMENTS

| | | | |
|---|---|---|---|
| 4,219,015 | 8/1980 | Steinemann | 606/69 |
| 4,297,993 | 11/1981 | Härle | 606/70 |
| 4,611,581 | 9/1986 | Steffee | 606/61 |
| 4,655,199 | 4/1987 | Steffee | 606/61 |
| 4,683,878 | 8/1987 | Carter | 606/69 |
| 4,696,290 | 9/1987 | Steffee | 606/61 |
| 4,790,297 | 12/1988 | Luque | 606/61 |
| 4,913,134 | 4/1990 | Luque | 606/61 |
| 4,957,496 | 9/1990 | Schmidt | 606/70 |
| 4,957,497 | 9/1990 | Hoogland | 606/71 |
| 5,002,544 | 3/1991 | Klaue | 606/69 |
| 5,084,049 | 1/1992 | Asher | 606/61 |

Primary Examiner—Robert A. Hafer
Assistant Examiner—Michael Brown
Attorney, Agent, or Firm—Woodard, Emhardt, Naughton, Moriarty & McNett

[57] ABSTRACT

A spinal fixation system includes a relatively rigid fixation plate which is engaged to a plurality of vertebrae by bone screws or bolts. The plate includes a longitudinal slot defined therethrough with an arrangement of scallops formed at the edge of the slot on the upper and lower surfaces of the plate. The scallop arrangement includes a first set of scallops formed at one spherical radius and a second set of scallops nested within the first that are formed at a smaller radius. Thus, the fixation plate can accommodate bone screws or bolts, or other bone engagement or load transmitting components having curved engagement surfaces of various diameters and providing varying degrees of rigidity. In another feature of the invention, a C-shaped ring is provided which encircles the plate to entrap the side walls of the plate, thereby restricting the plate walls from spreading as the bone screws or bolts are tightened onto the plate. The side walls of the plate and the inner walls of the C-shaped ring are correspondingly curved to retain the ring on the plate.

17 Claims, 3 Drawing Sheets

SPINAL FIXATION SYSTEM

BACKGROUND OF THE INVENTION

The present invention relates in general to spinal pedicular and interlaminal fixation systems useful for maintaining the vertebrae in a desired relationship. In particular, the invention concerns improvements to the spinal fixation system disclosed in U.S. Pat. Nos. 4,790,297 and 4,913,134 to Eduardo Luque and assigned to the assignee of the present invention.

Segmental spinal fusion plates with bolts and nuts have their genesis in 1948 through the work of Baker and Hoit. Since then, spinal fusion plates have become more sophisticated, as have the bolts and screws used to fix the plates to vertebrae. These fusion plates have been used to maintain certain vertebrae in rigid position relative to each other, for instance to facilitate fusion of a vertebra.

In the last decade, spinal fixation systems have been developed using generally rigid plates which span several vertebrae and are engaged on each side of the spinous process. One such type of spinal fixation system and rigid plate is illustrated in the patents to Steffee, U.S. Pat. Nos. 4,611,581 and 4,696,290. In this system, the spinal plate is provided with a series of openings for receiving the threaded portions of force transmitting members, such as bone screws. This spinal plate, known in the art as the Steffee plate, includes a number of bridge elements between each of the series of openings in the plate, which tend to increase the rigidity of the plate.

Another type of spinal fixation system is shown in the aforementioned patents to Luque, U.S. Pat. Nos. 4,790,297 and 4,913,134. In this system, a spinal fixation plate, known as the Luque plate, is described which includes a single elongated opening that extends substantially along the length of the plate. A number of scallops or depressions are formed in the top surface of the plate at the edge of the central opening. The scallops are used to engage a convex portion of a force-transmitting member, such as a bone screw. The system also includes plate ring means which prevents the plate from spreading when the bone screws are tightened down onto the scallops of the plate.

While the Luque system has proven very effective in spinal fixation, practitioners in the field of spinal implants have sought improvements to the system to render them more easily used and adapted to a variety of procedures. In addition, improvements to the systems have been sought to reduce the trauma to the vertebrae or surrounding tissue during and after implantation. While the need for improved usability and atraumatic characteristics is important, any improved system cannot sacrifice the essential beneficial performance of prior plate systems, such as the Luque system described in the above patents.

BRIEF DESCRIPTION OF THE DRAWINGS

FIG. 5b is an side elevational view of an alternative embodiment of a nut for use with the fixation bolt shown in FIG. 5a.

SUMMARY OF THE INVENTION

Figure 1A:
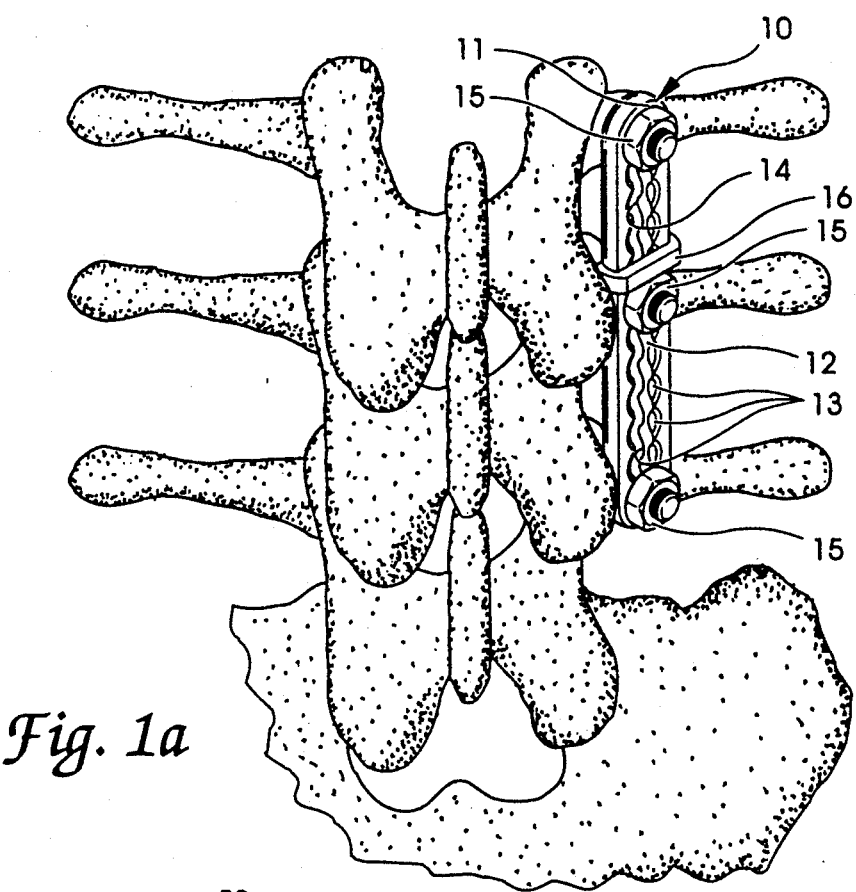
FIG. 1a is a pictorial plan view of a portion of a patient's spinal column with a spinal fixation system according to the Luque U.S. Pat. No. 4,790,297 on the right side of the vertebral column.

The present invention contemplates a spinal fixation system that incorporates the benefits of prior fixation plate type systems, while addressing some of the limitations of these systems. In particular, the system of this invention contemplates a fixation plate having a slot opening formed therethrough. The slot opening can extend substantially along the entire length of the plate, such as the Luque plate described in U.S. Pat. No. 4,790,297, or the opening can be segmented by bridge elements, such as the Steffee plate described in U.S. Pat. No. 4,611,581.

In one important feature, the plate includes scallop means formed at the edge of the slot opening which comprise, in the preferred embodiment, an arrangement of nested scallops. In this nested scallop configuration, one group of scallops is formed at one spherical radius and is nested within a second group of scallops formed at a larger spherical radius. Thus, the nested scallop configuration for the scallop means allows a bone screw or bolt to be alternatively used with a single plate. While the preferred embodiment envisions a nested scallop configuration, the large and small scallops can be arranged such that the scallops are only partially nested, or so that the scallops alternate along the plate slot opening.

In another aspect of the invention, a ring means is provided for controlling the outward deflection or spreading of the fixation plate as a bone engagement means or fastener, such as a bone screw, is tightened onto the plate. In the preferred embodiment, the ring means comprises a C-shaped body which encircles the fixation plate with side arms that entrap and restrain the side walls of the plate. The ring means includes a gap between the ends of the side arms which is smaller than the largest width dimension of the plate to retain the ring means around the plate. In a preferred embodiment, the side arms and side perimetrical walls of the plate are correspondingly curved.

It is one object of the present invention to provide a spinal fixation system using a relatively rigid plate and a number of bone engagement fasteners or load transmitting members, such as bone screws or bolts. A further object is to provide such a system which permits alternative use of either a screw or a bolt, or alternative use of components having a generally spherical engagement surface of different radius. Moreover, the invention achieves the ability to provide varying degrees of stiffness for a particular bone engagement fastener.

A further object resides in providing a fixation plate system which includes some means for restricting spreading of the plate walls when the bone engagement members are tightened onto the plate. Yet another object of this invention to provide such a means that has a reduced profile than prior such means and that is less traumatic to the vertebrae and surrounding tissue.

Other objects and certain benefits of the spinal fixation system of the present invention will be readily discerned by persons in the field of spinal fixation from consideration of the following written description and accompanying figures.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring first to FIG. 1a, a spinal fixation 10 according to the aforementioned Luque U.S. Pat. No. 4,790,297 is shown. The following description of this spinal fixation 10 is for illustrative and comparative purposes. A more detailed description of this system is found in the Luque '297 patent, which description is incorporated herein by reference. However, to summarize the features of this prior spinal fixation system 10, a substantially rigid spinal plate means 11, the Luque plate, is provided which is used for segmental fixation of the vertebrae V of a spinal column. The plate means includes a slot opening 12 therethrough which extends substantially along the length of the plate means. A lower surface 14 is adjacent to or in contact with at least two vertebrae V at the ends of the plate. A number of bone screw means 15 are provided for engaging a portion of a vertebra directly underneath, such as the pedicle of the vertebra. Means are provided to encircle or entrap the plate means 11 to prevent the side walls of the plate from spreading apart when bone screws are tightened down onto the plate. This means in the Luque '297 patent contemplates a component that encircles the plate means with the plate material either extending entirely across the underneath of the plate means or broken to form a gap in material beneath the plate means, provided the side walls of the plate are entrapped.

In one embodiment, a ring means 16 is provided which is of rectangular configuration having a rectangular opening to receive the plate means therethrough, as particularly shown in FIG. 12 of the Luque '297 patent and as described at column 3, lines 62-68 of that patent, which description has previously been incorporated by reference. In another embodiment (not shown) a body is provided which engages a bone screw and which also has a pair of flange portions to entrap the side walls of the plate means, as particularly shown in FIG. 15 of the '297 patent and as described at column 4, lines 1-13.

Figure 1B:
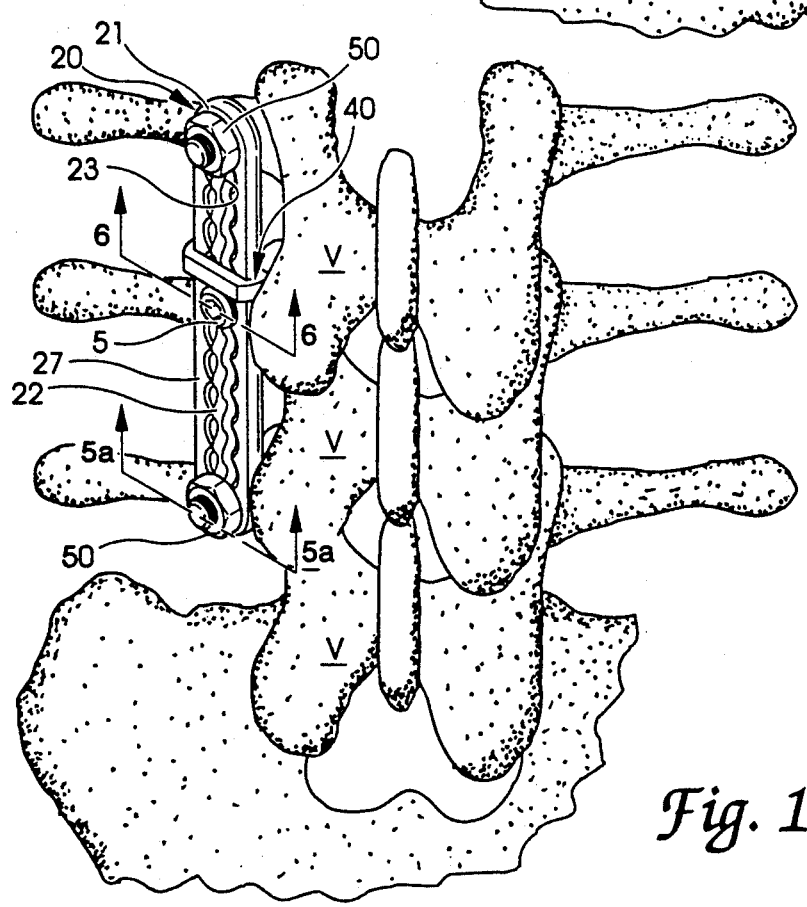
FIG. 1b is a pictorial plan view of a portion of a patient's spinal column with an improved spinal fixation system according to the present invention secured to the vertebra on the left side of the spinal column.

Referring now to FIG. 1b, on the opposite side of the spinous process is shown an improved fixation system 20 according to the present invention. This improved fixation system 20 includes a plate means 21 which is generally rigid and substantially similar in many respects to the prior Luque plate means 11 on the opposite side. The plate means 21 includes an elongated slot opening 22 which extends substantially along the entire length thereof. A lower surface 23 preferably abuts or is adjacent to at least two of the vertebrae V at the opposite ends of the plate means 21.

The plate means 21 is engaged to a vertebra V by way of force-transmitting members or fasteners, such as a first bone engagement means 50 and a second bone engagement means 51. For illustrative purposes, the bone engagement means have been separately designated as means 50 and 51 indicative that different bone engaging or force transmitting components may be employed with the improved fixation system 20 of the present invention. For instance, the first bone engagement means 50, as discussed in more detail herein, may be a bolt which includes a bone-engaging shank and a threaded post, each projecting from a generally spherical intermediate portion.

On the other hand, the second bone engagement means 51 may be a bone screw as shown in FIG. 10 of the Luque '297 patent and described at column 1, lines 28-60, which description has been previously incorporated by reference. It is understood that this second bone engagement means or bone screw 51 includes essentially a threaded bone-engaging shank and a head portion which is configured to engage scallops in a fixation plate. As described more fully in the Luque '297 patent, this second bone engagement means 51 does not include a threaded stem which extends through the slot opening 22 of the plate means 21. Rather, the head of the second bone engagement means 51 engages scallops in the upper surface 27 of the plate means 21 with the threaded shank extending through the slot opening 22 to engage the vertebra V.

Figure 2:
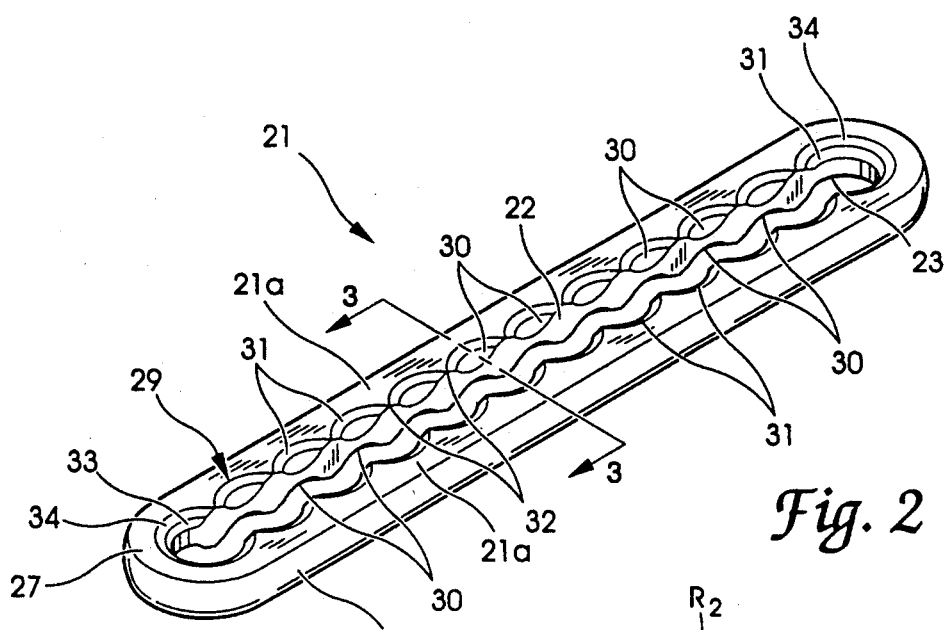
FIG. 2 is a perspective view of the fixation plate means of the spinal fixation system of the present invention.
Figure 3:
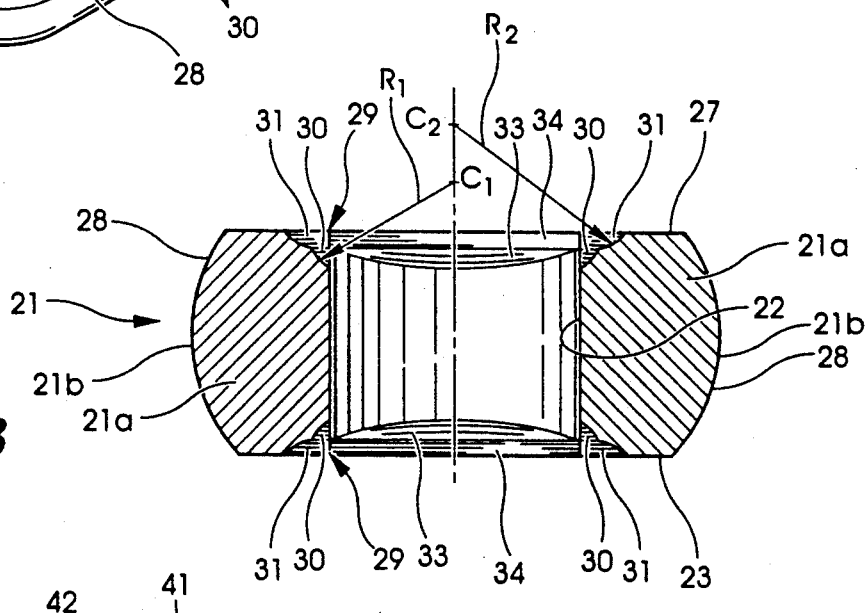
FIG. 3 is a transverse cross-sectional view of the fixation plate means shown in FIG. 2, taken along line 3—3 as viewed in the direction of the arrows.

Referring now to FIGS. 2 and 3, the details of the plate means 21 of the fixation system 20 of the present invention are shown. In particular, the plate means 21 is in the form of an elongated plate bounded by a lower surface 23 and upper surface 27 and a side perimetrical surface 28. A slot opening 22 is formed therethrough and extends substantially along the entire length of the plate means 21.

At the intersection between the slot opening 22 and the upper surface 27 is scallop means 29 comprising an arrangement of scallops or depressions. The scallop means 29 are provided to block sliding movement of one of the bone engaging means 50 or 51 relative to the plate means 21. In one important feature of the invention, the scallop means includes at least two sets of scallops formed at different spherical radii. In one embodiment, the two sets of scallops in means 29 are configured into nested pairs of scallops. In particular, a first set of scallops 30 is formed around the edge between the slot opening 22 and the upper surface 27. In this respect, the first scallop 20 are substantially similar to the scallops 13 of the prior fixation plate means 11 described in the Luque '297 patent. It is understood that each opposite edge of the slot opening 22 includes first scallops 30 which are aligned relative to each other across the slot opening.

In this embodiment, a second set of scallops 31 is provided which surrounds the first set of scallops 30, appearing concentric in planview. More specifically, the second scallops 31 are formed at a spherical radius $R_2$ which is larger than the spherical radius $R_1$ at which the first scallops 30 are formed. In other words, the first set of scallops 30 are cut deeper into the plate means than the second scallops 31. Consequently, the first scallops 30 are adapted to accommodate a mating fixation component which has a smaller spherical engagement surface. On the other hand, the second scallops 31 are adapted to engage a fixation component having a larger spherical surface or a shallower curved engagement surface.

Each of the set of scallops 30 and 31 terminates at the ends of the plate means 21 in end scallops. Specifically, a first end scallop 33 is formed at each end of the plate and is nested within a second end scallop 34 having a larger spherical radius. It is understood that the same scallop means 29, or nested arrangement of scallops 30 and 31, can be formed at the lower surface 23 of the plate means 21.

While the preferred embodiment contemplates nested pairs of scallops 30 and 31, other arrangements of the scallops are contemplated. For instance, the scallops can be only partially nested with the smaller scallops 30 longitudinally offset from the larger scallops 31. In another variation, the scallops are not nested but interspersed along the length of the slot opening.

One benefit of the present invention is that the provision of two sets of scallops of different spherical radii permit the use of different bone engagement means having different fixation stiffness properties. For instance, it is known that bone bolts typically provide a stiffer fixation, and therefor greater load transmission, between the vertebra and the plate means, than spinal fixation screws. The bone bolts provide engagement on both sides of the plate means to more rigidly hold the bolt to the plate than the screw, which contact only the upper surface of the plate. However, a "spring" effect can be provided in the use of bone bolts having a smaller spherical radius of contact to the plate means. A larger spherical radius of contact provides a significant increase in bolt/plate means interface rigidity. Frequently, spinal implants require varying degrees of fixation between the vertebra and the fixation plate. The present invention provides a means for accommodating this need. One benefit of this nested-scallop feature of the preferred embodiment is the greater adjustability of the position of the bone engagement means permitted along the length of the plate means.

Figure 5A:
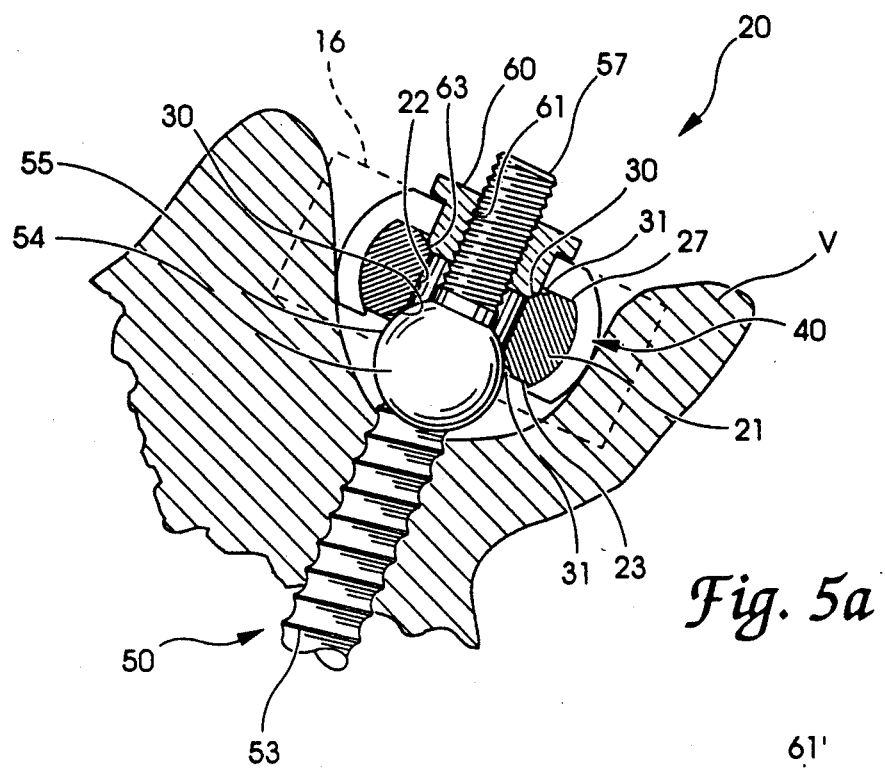
FIG. 5a is an enlarged sectional view of a vertebra with the spinal fixation system of the present invention attached thereto, and in particular a cross-sectional view taken along 5—5 in FIG. 1b as viewed in the direction of the arrows, showing a fixation bolt.

Referring to FIG. 5a, a first bone engagement means 50 is shown extending through the slot opening 22 of the plate means 21. In particular, this first bone engagement means 50 is a bone bolt having a threaded shank 53 adapted to engage the pedicle of the vertebra V. The upper end of the threaded shank 53 merges into an intermediate portion 54 which includes a curved plate engagement surface 55 that is generally spherical in shape. This curved surface 55, at least in this specific embodiment, has a spherical radius adapted to engage one of the first set of scallops 30 which has a smaller spherical radius than the outboard scallops 31.

This first bone engagement means 50 also includes a threaded stem which projects from the intermediate portion 54 in a direction opposite the threaded shank 53. With the intermediate portion 54 engaging the lower surface 23 of the plate means 21, the threaded stem 57 extends through the slot opening 22 and beyond the opposite upper surface 27 of the plate means. A nut 60 which includes a threaded bore 61 is adapted to engage the threaded stem 57. By tightening the nut 60 onto the threaded stem 57, the bone bolt or first bone engagement means 50 is secured to the plate means 21 even as the threaded shank 53 is engaged in a pedicle of the vertebra V.

In this specific embodiment, the nut 60 includes a lower plate engagement surface 63 which has the same curvature as the curved surface 55 of the intermediate portion 54. Thus, the nut 60 and particularly the lower engagement surface 63 will reside within one of the second set of scallops 30 having the smaller spherical radius.

Figure 5B:
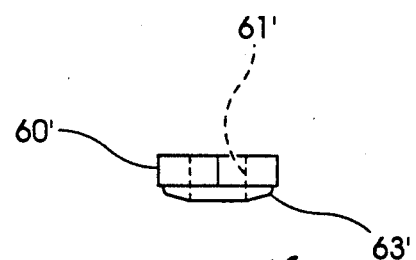

Alternatively, the nut can be constructed as nut 60' shown in FIG. 5b. The nut 60' has a lower engagement surface 63' which is shallower or formed at a larger spherical radius than the surface 63 shown in FIG. 5a. Typically, the curvature of the curved surface 55 of the bone bolt intermediate portion 54 would be the same as the surface 63', so that both the bone bolt and the nut would engage the same larger radii scallops 31 in the fixation plate means 21. It should be apparent that the present invention permits the fixation to the same plate means of bone bolts having different interface rigidities. The bolt 50 and nut 60 combination shown in FIG. 5a would provide the lesser rigidity, while the use of nut 60' shown in FIG. 5b and a correspondingly configured bolt would provide greater rigidity because the components engage the larger, shallower radii scallops 31.

Figure 6:
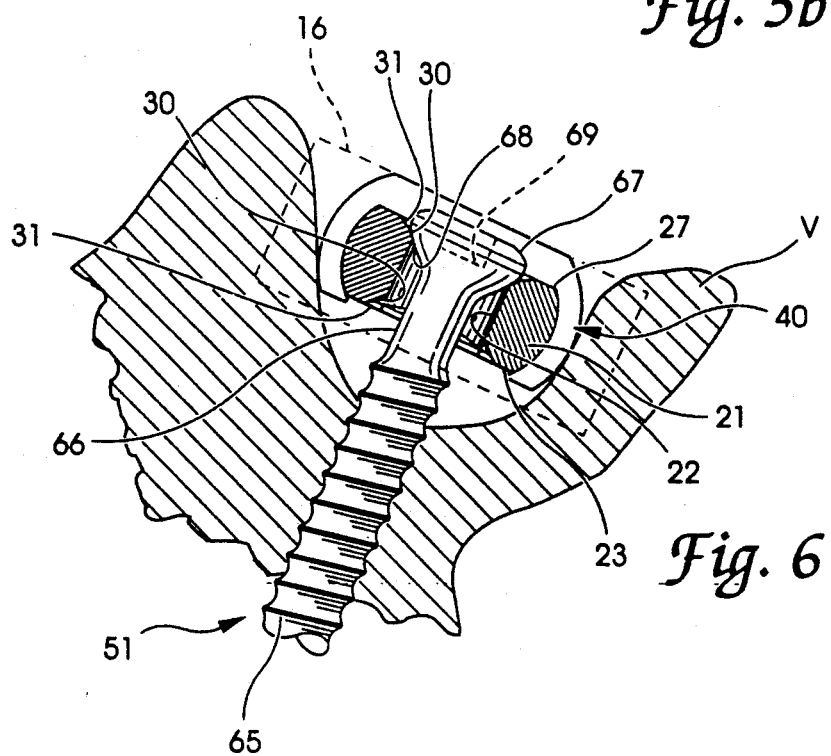
FIG. 6 is an enlarged sectional view of a vertebra with the spinal fixation system of the present invention attached thereto, and in particular a cross-sectional view taken along line 6—6 in FIG. 1b as viewed in the direction of the arrows, showing a fixation screw.

In practice, a second bone engagement means 51, which as a bone screw, would be utilized when less rigidity, or more flexibility is required in the fixation plate/vertebra load transmitting interface. The bone screw 51 contacts the plate mean 21 only at the upper surface 27, so that the plate is not sandwiched between fixation components as in FIG. 5a. As shown more clearly in FIG. 6, bone screw of second bone engagement means 51 includes a threaded shank 65 threaded to engage the pedicle, for example. The thread shank 65 terminates at an upper cylindrical portion 66, which is integral with the screw head 67. The screw head 67 includes a lower engagement surface 68 which is curved to engage one of the scallops in the scallop means 29. In the specific embodiment, the engagement surface 68 is curved to engage the smaller scallops 30 to provide the greatest amount of flexibility in the screw/plate interface. (If somewhat less flexibility is desired, the engagement surface 68 can be formed at a larger radius to engage the shallower scallops 31.) The head 67 includes a hex-configured recess to receive a tool for driving the bone screw 51 into the vertebra.

While a bone screw 51 has been depicted in the preferred embodiment, essentially the same flexibility can be achieved by using the bone bolt 50 described above as a bone screw. In other words, the bone bolt 50 can extend through the slot opening 22 so that the lower part of the spherical intermediate portion 54 contacts the upper surface 27 of the plate means 20.

It can be envisioned that a spinal fixation system of the present invention when implanted into a patient may include first bone engagement means 50, or bone bolts, situated at opposite ends of the bone plate means 21 which would be engaged within the larger second scallops 31 of the plate means to provide the greatest possible fixation rigidity. At the same time, a second bone engagement means 51, or bone screw, could be disposed intermediate the ends of the plate means 21 which has a point of engagement with the smaller first scallops 30 of the plate means 21 to permit a greater "spring" effect in the fixation. Which of the nested scallops 30 or 31 is used can be determined by the relative rigidity required for fixing the bone engagement means with the plate. It should be apparent then that the nested-scallop configuration of the plate means 21 of the present invention increases the flexibility of use of the spinal fixation 20 of this invention over prior fixation systems which have but a single scallop dimension throughout the entire plate.

Referring again to FIG. 1b, it is seen that the improved fixation system 20 also includes a ring means 40 which encircles the plate means 21 to entrap the side walls 21a to restrict spreading of the side walls as the bone engagement means is tightened onto the plate. For instance, as the nut 60 of first bone engagement means 50 is tightened down, the curved surfaces 55 and 63 contacting the plate are drawn together which tends to spread the side walls 21a. If the side walls spread too much, the rigidity of the fixation is compromised. Thus, the ring means 40 tends to protect the rigidity of the fixation system while permitting some "working" of the plate/bone screw union.

Figure 4:
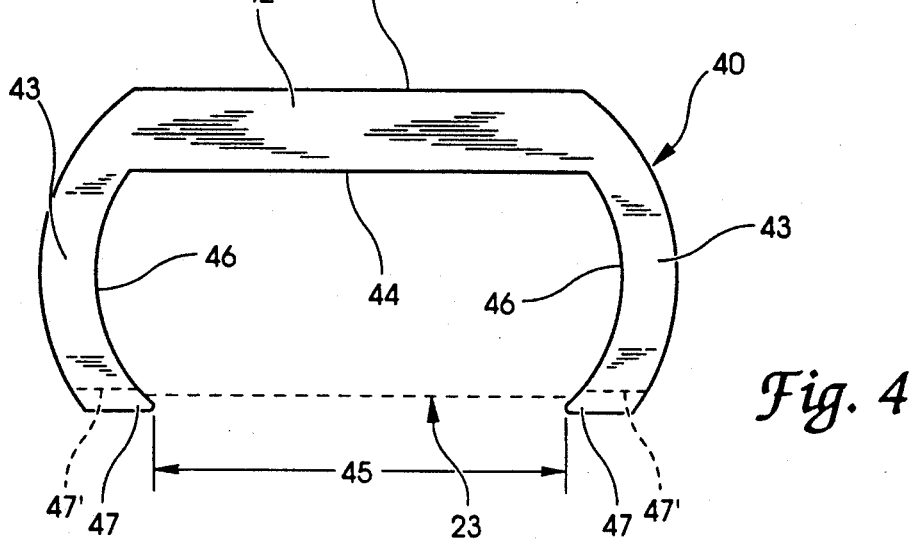
FIG. 4 is a side elevational view of the ring means of the present invention shown as used in connection with the spinal fixation system in FIG. 1b.

The details of the ring means 40 are shown more clearly in FIG. 4. In this figure it is seen that the ring means 40 of the present invention includes a generally C-shaped body 41 which comprises an upper bar 42 from which extends a pair of opposite curved side arms 43. A plate opening 44 is provided between the upper and side arms to receive the plate means 21 therethrough. The side arms 43 also define a gap 45 therebetween which opens into the plate opening 44. The ring means 40 can be readily installed on the plate means 21 prior to implantation by sliding the plate means 21 through the plate opening 44 of the C-shaped body 41.

In an important aspect of the ring means 40 of the present invention, the side arms 43 each include a curved inner engagement surface 46. These curved inner engagement surfaces 46 are configured to contact the similarly curved side perimetrical surfaces 28 of the plate means 21 (see FIG. 3). Thus, as shown more clearly in FIG. 5a, the ring means 40 encircles the plate means 21 with the inner engagement surfaces 46 of the side arms 43 contacting or adjacent the opposite side surfaces 28 of the plate means 21. The coincident curvatures of the side surfaces 28 and the engagement surfaces 46 of the side arms 43 prevent the ring means 40 from being removed from the plate means 21, at least once the fixation system 20 has been implanted. More specifically, the gap 45 between the ends of the side arms 43 has a width less than the greatest width of the plate means, which in the preferred embodiment is at the apexes 21b of the curved perimetrical surfaces 28.

As shown in FIG. 5a, the lower end 47 of each of the side arms 43 projects below the lower surface 23 (shown in phantom lines in FIG. 4) of the plate means 21. However, the lower end of the side arms need not project below the lower surface of the plate, and instead may terminate at a location 47'(FIG. 4) which is above the lower surface 23 of the plate. It has been found that this configuration of the ring means 40 reduces the amount of trauma caused by the ring means to the vertebrae and surrounding tissue of the patient. In addition, this ring means 40 can alleviate void and stress problems that could arise in vertebral bone graft procedures with prior ring means. It is important, however, that the gap 45 between the ends of the side arms, whether at location 47 or 47', be narrower than the greatest width of the plate means 20, such as between apexes 21b.

As can be seen in FIG. 5a, the envelope occupied by the ring means 16 of the prior art fixation system 10, as depicted in phantom lines, is larger than the envelope occupied by the ring means 40 of the present invention. Thus, the ring means 40 is less likely to contact or traumatize surrounding tissue. At the same time, the ring means substantially encircles the plate means 21 to prevent the plate means from bellowing outward as the bone engagement means 50 and 51 are tightened onto the plate.

In one specific embodiment of the invention, plate means 21 has a length between 30.0 and 160.0 mm, depending upon the particular application and the number of vertebrae to be spanned. The scallops 30 and 31 are distributed at approximately 5.0 mm intervals. The first set of scallops 30 are formed at a spherical radius $R_1$ of approximately 4.0 mm from a centroid $C_1$ approximately 0.4 mm above the surface of the plate means. The larger second scallops 31 are formed at a spherical radius $R_2$ of about 10.0 mm from a centroid $C_2$ about 8.7 mm above the plate. The slot opening 22 in this specific embodiment has a width of about 6.6 mm. With these specific dimensions, a series of intermediate flats 32 are defined between each of the first scallops 30. The larger second scallops 31 in the illustrated specific embodiment generally overlap into each other along the length of the slot opening 22 of the plate means 21. (However, in an alternative embodiment, the smaller scallops 30 are situated where the flats 32 are located in the illustrated embodiment, that is between the larger second scallops 31.) The plate means 21 of this specific embodiment includes identically configured first and second scallops on both the upper surface 27 and lower surface 23.

As to the ring means feature of the present invention, the C-shaped body 41 is adapted to engage a plate means 21 having a width of approximately 14.0 mm, thus the maximum distance between the inner engagement surfaces 46 of the opposite side arms 43 must be at least 14.0 mm. On the other hand, the width of gap 45 is less than the plate means width, having a dimension in this specific embodiment of 13.0 mm. The curvature of the side perimetrical surface 28 of the plate means 21 is approximately at a radius of 4.75 mm, while the curvature of the inner engagement surfaces 46 is slightly larger at about 4.95 mm radius. The edges of the ring means body 41 are preferably rounded to minimize tissue trauma.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, while the preferred embodiment has been described as a modification of the known Luque plate, the inventive features can be incorporated into other the known fixation plates having one or multiple slots, or into fixation plates where it is desirable to restrict spreading of the plate side walls as the bone engagement components are tightened down.

What is claimed is:

1. An apparatus for use with bone engaging fasteners for maintaining the vertebrae in a desired relationship, comprising:

substantially rigid plate means for being placed over the vertebrae, said plate means having a lower surface for facing the vertebrae and an opposite upper surface;

a number of slot openings defined through said plate means between said upper surface and said lower surface, each of said number of slot openings being sized to receive a bone engaging fastener therethrough; and scallop means for blocking sliding movement of a bone engaging fastener relative to said plate means, said scallop means including a first set of scallops and a second set of scallops, each set of scallops being formed by a number of depressions defined in at least one of said lower surface and said upper surface of said plate across said number of slot openings, wherein said first set of scallops is defined at a spherical radius that is different from said second set of scallops.

2. The apparatus of claim 1, wherein said scallop means further includes each of said first set of scallops and said second set of scallops formed by a number of depressions defined in both of said lower surface and said upper surface of said plate at said number of slot openings.

3. The apparatus of claim 1, wherein said first set of scallops is nested within said second set of scallops.

4. An apparatus for use with bone engaging fasteners for maintaining the vertebrae in a desired relationship, comprising:

substantially rigid plate means for being placed over the vertebrae, said plate means having a lower surface for facing the vertebrae and an opposite upper surface;

a number of slot openings defined through said plate means between said upper surface and said lower surface, each of said number of slot openings being sized to receive a bone engaging fastener therethrough; and scallop means for blocking sliding movement of a bone engaging fastener relative to said plate means, said scallop means including a first set of scallops and a second set of scallops, each set of scallops being formed by a number of depressions defined in at least one of said lower surface and said upper surface of said plate at said number of slot openings, wherein said first set of scallops is defined at a spherical radius that is different from said second set of scallops, wherein for said first set of scallops each of said number of depressions is defined at a first spherical radius, and for said second set of scallops each of said number of depressions is defined at a second spherical radius greater than said first spherical radius.

5. The apparatus of claim 4, wherein:

said first spherical radius is defined from a first centroid which is at a first distance from said at least one of said lower surface and upper surface of said plate; and said second spherical radius is defined from a second centroid which is at a second distance from said at least one of said lower surface and upper surface of said plate, said second distance being greater than said first distance.

6. The apparatus of claim 5, wherein said second distance is greater than said first spherical radius.

7. An apparatus for use with bone engaging fasteners for maintaining the vertebrae in a desired relationship, comprising:

substantially rigid plate means for being placed over the vertebrae, said plate means having a lower surface for facing the vertebrae and an opposite upper surface;

a number of slot openings defined through said plate means between said upper surface and said lower surface, each of said number of slot openings being sized to receive a bone engaging fastener therethrough; and scallop means for blocking sliding movement of a bone engaging fastener relative to said plate means, said scallop means including a first set of scallops and a second set of scallops, each set of scallops being formed by a number of depressions defined in at least one of said lower surface and said upper surface of said plate at said number of slot openings, wherein said first set of scallops is defined at a spherical radius that is different from said second set of scallops.

wherein said first set of scallops is nested within said second set of scallops, and further wherein for said first set of scallops each of said number of depressions is defined at a first spherical radius, and for said second set of scallops each of said number of depressions is defined at a second spherical radius greater than said first spherical radius.

8. The apparatus of claim 7, wherein:

said first spherical radius is defined from a first centroid which is at a first distance from said at least one of said lower surface and upper surface of said plate; and said second spherical radius is defined from a second centroid which is at a second distance from said at least one of said lower surface and upper surface of said plate, said second distance being greater than said first distance.

9. The apparatus of claim 8, wherein said second distance is greater than said first spherical radius.

10. An apparatus for maintaining the vertebrae in a desired relationship, comprising:

a substantially rigid plate for being placed over the vertebrae, said plate having an lower surface for facing the vertebrae and an opposite upper surface;

a first bone engaging fastener for connecting said plate to the vertebrae and having a first plate engaging portion;

a second bone engaging fastener for connecting said plate to the vertebrae and having a second plate engaging portion;

said plate including a number of elongated slot openings defined therethrough between said upper and lower surfaces, each of said number of slot openings being sized to receive each of said pair of bone engaging fasteners therethrough; and scallop means for blocking sliding movement of a bone engaging fastener relative to said plate, said scallop means including a first set of scallops and a second set of scallops, each set of scallops being formed by a number of depressions defined in at least one of said upper surface and said lower surface of said plate across said number of slot openings for receiving said plate engaging portion of each of said pair of bone engaging fasteners, wherein said first set of scallops is defined at a spherical radius that is different from said second set of scallops.

11. An apparatus for maintaining the vertebrae in a desired relationship, comprising:
   a substantially rigid plate for being placed over the vertebrae, said plate having an lower surface for facing the vertebrae and an opposite upper surface;
   a first bone engaging fastener for connecting said plate to the vertebrae and having a first plate engaging portion;
   a second bone engaging fastener for connecting said plate to the vertebrae and having a second plate engaging portion;
   said plate including a number of elongated slot openings defined therethrough between said upper and lower surfaces, each of said number of slot openings being sized to receive each of said pair of bone engaging fasteners therethrough; and
   scallop means for blocking sliding movement of a bone engaging fastener relative to said plate, said scallop means including a first set of scallops and a second set of scallops, each set of scallops being formed by a number of depressions defined in at least one of said upper surface and said lower surface of said plate at said number of slot openings for receiving said plate engaging portion of each of said pair of bone engaging fasteners, wherein said first set of scallops is defined at a spherical radius that is different from said second set of scallops.
   wherein said first plate engaging portion of said first bone engaging fastener is formed at a first spherical radius, and said second plate engaging portion of said second bone engaging fastener is defined at a second spherical radius greater than said first spherical radius.

12. An apparatus for maintaining the vertebrae in a desired relationship, comprising:
   a substantially rigid plate for being placed over the vertebrae, said plate having an lower surface for facing the vertebrae and an opposite upper surface;
   a pair of bone engaging fasteners for connecting said plate to the vertebrae;
   said plate including a pair of opposite side walls defining a number of elongated slot openings therebetween, said slot openings extending through said plate between said upper and lower surfaces, each of said number of slot openings being sized to receive each of said pair of bone engaging fasteners therethrough;
   each of said fasteners including means for tightening the fasteners against said plate between said side walls; and
   ring means for encircling said plate to preventing said side walls of said plate from spreading apart when one of said bone engaging fasteners is tightened down onto said plate, said ring means including an upper portion spanning said slot openings and a pair of opposite arms extending therefrom adjacent each of said side walls of said plate and defining a gap between one end of each of said arms, said gap having a dimension less than the greatest width dimension of said plate at said side walls.

13. The apparatus of claim 12, wherein said ring means includes a C-shaped body including said pair of opposite arms.

14. The apparatus of claim 12, wherein:
   each of said side walls have a curved outer surface; and
   each of said opposite arms have a curved inner surface corresponding to said curved outer surface of each of said side walls.

15. The apparatus of claim 12, wherein said one end of each of said opposite arms projects beyond said bottom surface of said plate when said ring means is encircling said plate.

16. The apparatus of claim 12, wherein said one end of each of said opposite arms do not project beyond said bottom surface of said plate when said ring means is encircling said plate.

17. The apparatus of claim 12, further comprising:
   scallop means for blocking sliding movement of a bone engaging fastener relative to said plate, said scallop means including a set of scallops being formed by a number of depressions defined in at least one of said upper surface and said lower surface of said plate at said number of slot openings for receiving one of said pair of bone engaging fasteners.

* * * * *